United States Patent
Bellet et al.

(10) Patent No.: US 6,514,708 B2
(45) Date of Patent: Feb. 4, 2003

(54) PROCESS FOR DETECTING THE MALIGNANT TRANSFORMATION OF HUMAN CELLS

(75) Inventors: Dominique Bellet, Paris (FR); Jean-Michel Bidart, Sceaux (FR); Michel Vidaud, Paris (FR); Vladimir Lazar, Villejuif (FR)

(73) Assignee: Institut Gustave Roussy, Villejuif (FR)

( * ) Notice: Subject to any disclaimer, the term of this patent is extended or adjusted under 35 U.S.C. 154(b) by 11 days.

(21) Appl. No.: 09/760,294

(22) Filed: Jan. 16, 2001

(65) Prior Publication Data

US 2002/0192646 A1 Dec. 19, 2002

Related U.S. Application Data

(63) Continuation of application No. 09/142,320, filed as application No. PCT/FR97/00361 on Feb. 28, 1997, now Pat. No. 6,194,154.

(30) Foreign Application Priority Data

Mar. 4, 1996 (FR) .............................. 96 02683

(51) Int. Cl.$^7$ .......................... G01N 33/53; C07K 1/00; C07K 16/00
(52) U.S. Cl. ...................... 435/7.1; 530/350; 530/387.1
(58) Field of Search ..................... 435/6, 91.1, 7.1; 530/350, 387.1

(56) References Cited

FOREIGN PATENT DOCUMENTS

WO          94/20859       9/1994

OTHER PUBLICATIONS

Lockhart et al., Nature, vol. 405, pp 827–836; (2000).*
Marcillac et al., Cancer Research; vol. 52, pp 3901–3907; 1992.*

V. Lazar et al., "Cancer Research", *Expression of Human Chorionic Gonadotrophin Beta Subunit Genes in Superficial and Invasive Bladder Carcinomas*, vol. 55, No. 17, pp. 3735–3738, (Sep. 1, 1995).

G.H. Cotton, "The Biochemical Journal", *Detection of Single Base Changes in Nucleic Acids*, vol. 263, pp. 1–10, (Oct. 1989).

F. Housseau et al., "International Journal of Cancer", *Reaction of Peripheral Blood Lymphocytes to the Human Chorionic Gonadotrophin Beta Sub–Unit in Patients with Productive Tumors*, vol. 63, pp. 633–638, (Nov. 27, 1995).

J. Bidart et al., Trends in Endocrinol. Metabolism, *Human Chorionic Gonadotrophin: Molecular Forms, Detection, and Clinical Implications*, vol. 4, No. 9, pp. 285–291, (Nov. 1993).

D. Bellet et al., "Cancer Research", *Malignant Transformation of Nontrophoblastic Cells is Associated with the Expression of Chorionic Gonadotropin Beta Genes Normally Transcribed in Trophoblastic Cells*, vol. 57, (Jan. 1997).

Forough et al (1993) J. Biol. Chem. 268: 2960–2968.

Andreadis et al (1987) Ann. Rev. Cell Biol. 3: 207–242.

* cited by examiner

*Primary Examiner*—W. Gary Jones
*Assistant Examiner*—Jehanne Souaya
(74) *Attorney, Agent, or Firm*—Foley & Lardner

(57) ABSTRACT

A process for detecting malignant transformation of cells involves detecting the overexpression of the products of the β3, β5, β8 and β9 genes, which encode the hCGβ subunit, relative to their expression in nonmalignant cells. A kit for diagnosing an hCG- or an hCG fragment-secreting cancer includes an assembly of polypeptides covering at least a part of the primary sequence of hCG. The use of a polypeptide corresponding to at least one portion of the primary sequence of hCG for producing a composition useful in hCG- or hCG fragment-secreting cancer immunotherapy is also disclosed.

6 Claims, 4 Drawing Sheets

COMPARISON OF THE NUCLEOTIDE SEQUENCES OF THE cDNAs OF
THE hCG-beta genes

```
Consensus   TCCAGCACYT TBCTCGGGTC ACGGCCTCCT CCTGGYTYCC ARGACCCCAC   50
p-beta-7    ........C. .T........ .......... .....T.C... .A........   50
p-beta-6    ........T. .C........ .......... .....T.C... .A........   50
p-beta-9    ........C. .T........ .......... .....C.C... .G........   50
p-beta-8    ........C. .T........ .......... .....C.C... .G........   50
p-beta-5    ........T. .G........ .......... .....C.C... .G........   50
p-beta-3    ........T. .G........ .......... .....C.T... .A........   50

Consensus   CATAGGCAGA GGCAGGCCTT CCTACACCCT ACTCYCTGTG CCTCCAGSCT  100
p-beta-7    .......... .......... .......... ....T..... .......C..  100
p-beta-6    .......... .......... .......... ....T..... .......C..  100
p-beta-9    .......... .......... .......... ....C..... .......C..  100
p-beta-8    .......... .......... .......... ....C..... .......G..  100
p-beta-5    .......... .......... .......... ....C..... .......G..  100
p-beta-3    .......... .......... .......... ....C..... .......C..  100

Consensus   YGACTAGTCC CTARCACTCG ACGACTGAGT CTCWGAGRTC ACTTCACCGT  150
p-beta-7    C......... ...G...... .......... ...A...G.. ..........  150
p-beta-6    C......... ...A...... .......... ...A...G.. ..........  150
p-beta-9    C......... ...G...... .......... ...T...G.. ..........  150
p-beta-8    T......... ...G...... .......... ...T...G.. ..........  150
p-beta-5    C......... ...G...... .......... ...T...A.. ..........  150
p-beta-3    C......... ...G...... .......... ...T...G.. ..........  150

Consensus   GGTCTCCGCC TCAYCCTTGG YGCTRGACCA STGAGRGGAG AGGRCTGGGG  200
p-beta-7    .......... ...T...... T...A..... C....G.... ...A......  200
p-beta-6    .......... ...T...... C...A..... C....G.... ...A......  200
p-beta-9    .......... ...C...... C...G..... G....A.... ...G......  200
p-beta-8    .......... ...C...... C...G..... G....A.... ...G......  200
p-beta-5    .......... ...C...... C...G..... G....A.... ...G......  200
p-beta-3    .......... ...C...... C...G..... C....G.... ...G......  200

Consensus   YGCTCCGCTG AGCCACTCCT GHGCCYCCST GGCCTTGTCT ACYTCTYGCC  250
p-beta-7    T......... .......... .T...T..C. .......... ..T...C...  250
p-beta-6    T......... .......... .T...T..C. .......... ..T...C...  250
p-beta-9    C......... .......... .C...C..C. .......... ..C...T...  250
p-beta-8    C......... .......... .C...C..C. .......... ..C...T...  250
p-beta-5    C......... .......... .C...C..C. .......... ..C...T...  250
p-beta-3    C......... .......... .A...C..G. .......... ..C...T...  250

Consensus   CCCCRARGGG TTAGTGTCSA GCTCACYCCA GCATCCTAYM ACCTCCTGGT  300
p-beta-7    ....G.A... ........C. ......T... ........CA ..........  300
p-beta-6    ....G.A... ........G. ......T... ........CA ..........  300
p-beta-9    ....G.G... ........G. ......C... ........TC ..........  300
p-beta-8    ....G.A... ........G. ......T... ........CA ..........  300
p-beta-5    ....G.A... ........G. ......C... ........CA ..........  300
p-beta-3    ....A.G... ........G. ......C... ........CC ..........  300

Consensus   GGCCTTGMCG CCCCCACAAM CCCGAGGTWT RAAGCCAGGT ACACSAGGCA  350
p-beta-7    ........A. ........A. ........A. A......... ....C.....  350
p-beta-6    .....C... ........C. ........A. G......... ....C.....  350
p-beta-9    .....C... ........C. ........A. A......... ....G.....  350
p-beta-8    .....C... ........C. ........T. A......... ....G.....  350
p-beta-5    .....C... ........C. ........A. A......... ....G.....  350
p-beta-3    .....C... ........C. ........A. A......... ....G.....  350
```

FIGURE 1a

COMPARISON OF THE NUCLEOTIDE SEQUENCES OF THE cDNAs OF
THE hCG-beta genes

```
Consensus    GGGGACRCAC CAAGGATGGA GATGTTCCAG GGGCTGCTGC TGTTGCTGCT    400
p-beta-7     ......G...  .......... .......... .......... ..........    400
p-beta-6     ......G...  .......... .......... .......... ..........    400
p-beta-9     ......G...  .......... .......... .......... ..........    400
p-beta-8     ......A...  .......... .......... .......... ..........    400
p-beta-5     ......G...  .......... .......... .......... ..........    400
p-beta-3     ......G...  .......... .......... .......... ..........    400

Consensus    GCTGAGCATG GGCGGGACAT GGGCATCCAR GGAGMYRCTT CGGCCACGGT    450
p-beta-7     .......... .......... ........G. ....ATG... ..........    450
p-beta-6     .......... .......... ........A. ....CCA... ..........    450
p-beta-9     .......... .......... ........A. ....CCG... ..........    450
p-beta-8     .......... .......... ........A. ....CCG... ..........    450
p-beta-5     .......... .......... ........A. ....CCG... ..........    450
p-beta-3     .......... .......... ........A. ....CCG... ..........    450

Consensus    GCCGCCCCAT CAATGCCACC CTGGCTGTGG AGAAGGAGGG CTGCCCCGTG    500
p-beta-7     .......... .......... .......... .......... ..........    500
p-beta-6     .......... .......... .......... .......... ..........    500
p-beta-9     .......... .......... .......... .......... ..........    500
p-beta-8     .......... .......... .......... .......... ..........    500
p-beta-5     .......... .......... .......... .......... ..........    500
p-beta-3     .......... .......... .......... .......... ..........    500

Consensus    TGCATCACCG TCAACACCAC CATCTGTGCC GGCTACTGCC CCACCATGAC    550
p-beta-7     .......... .......... .......... .......... ..........    550
p-beta-6     .......... .......... .......... .......... ..........    550
p-beta-9     .......... .......... .......... .......... ..........    550
p-beta-8     .......... .......... .......... .......... ..........    550
p-beta-5     .......... .......... .......... .......... ..........    550
p-beta-3     .......... .......... .......... .......... ..........    550

Consensus    CCGCGTGCTG CAGGGGGTCC TGCCGGCCCT GCCTCAGGTG GTGTGCAACT    600
p-beta-7     .......... .......... .......... .......... ..........    600
p-beta-6     .......... .......... .......... .......... ..........    600
p-beta-9     .......... .......... .......... .......... ..........    600
p-beta-8     .......... .......... .......... .......... ..........    600
p-beta-5     .......... .......... .......... .......... ..........    600
p-beta-3     .......... .......... .......... .......... ..........    600

Consensus    ACCGCGATGT GCGCTTCGAG TCCATCCGGC TCCCTGGCTG CCCGCGCGGC    650
p-beta-7     .......... .......... .......... .......... ..........    650
p-beta-6     .......... .......... .......... .......... ..........    650
p-beta-9     .......... .......... .......... .......... ..........    650
p-beta-8     .......... .......... .......... .......... ..........    650
p-beta-5     .......... .......... .......... .......... ..........    650
p-beta-3     .......... .......... .......... .......... ..........    650

Consensus    GTGAACCCCG TGGTCTCCTA CGCCGTGGCT CTCAGCTGTC AATGTGCACT    700
p-beta-7     .......... .......... .......... .......... ..........    700
p-beta-6     .......... .......... .......... .......... ..........    700
p-beta-9     .......... .......... .......... .......... ..........    700
p-beta-8     .......... .......... .......... .......... ..........    700
p-beta-5     .......... .......... .......... .......... ..........    700
p-beta-3     .......... .......... .......... .......... ..........    700
```

FIGURE 1b

COMPARISON OF THE NUCLEOTIDE SEQUENCES OF THE cDNAs OF THE hCG-beta genes

```
Consensus   CTGCCGCCGC AGCACCACTG ACTGCGGGGG TCCCAAGGAC CACCCCTTGA    750
p-beta-7    .......... .......... .......... .......... ..........    750
p-beta-6    .......... .......... .......... .......... ..........    750
p-beta-9    .......... .......... .......... .......... ..........    750
p-beta-8    .......... .......... .......... .......... ..........    750
p-beta-5    .......... .......... .......... .......... ..........    750
p-beta-3    .......... .......... .......... .......... ..........    750

Consensus   CCTGTGATGA CCCCCGCTTC CAGGMCTCCT CTTCCTCAAA GGCCCCTCCC    800
p-beta-7    .......... .......... ....C..... .......... ..........    800
p-beta-6    .......... .......... ....C..... .......... ..........    800
p-beta-9    .......... .......... ....A..... .......... ..........    800
p-beta-8    .......... .......... ....A..... .......... ..........    800
p-beta-5    .......... .......... ....A..... .......... ..........    800
p-beta-3    .......... .......... ....A..... .......... ..........    800

Consensus   CCSAGCCTTC CAAGYCCATC CCGACTCCCG GGGCCCTCGG ACACCCCGAT    850
p-beta-7    ..C....... ....T..... .......... .......... ..........    850
p-beta-6    ..C....... ....T..... .......... .......... ..........    850
p-beta-9    ..C....... ....C..... .......... .......... ..........    850
p-beta-8    ..C....... ....T..... .......... .......... ..........    850
p-beta-5    ..C....... ....T..... .......... .......... ..........    850
p-beta-3    ..G....... ....T..... .......... .......... ..........    850

Consensus   CCTCCCACAA TAAAGGCTTC TCAATCCGCA CTCTGGMGGT GTC            893
p-beta-7    .......... .......... .......... ......A... ...            893
p-beta-6    .......... .......... .......... ......A... ...            893
p-beta-9    .......... .......... .......... ......C... ...            893
p-beta-8    .......... .......... .......... ......A... ...            893
p-beta-5    .......... .......... .......... ......A... ...            893
p-beta-3    .......... .......... .......... ......C... ...            893
```

FIGURE 1c

COMPARISON OF THE SEQUENCES OF THE MATURE hCG-beta PROTEINS

| | | | | | | |
|---|---|---|---|---|---|---|
| Consensus | SKEPLRPRCR | PINATLAVEK | EGCPVCITVN | TTICAGYCPT | MTRVLQGVLP | 50 |
| Trans of p-beta-7 | .R.M...... | .......... | .......... | .......... | .......... | 50 |
| Trans of p-beta-8 | .......... | .......... | .......... | .......... | .......... | 50 |
| Trans of p-beta-9 | .......... | .......... | .......... | .......... | .......... | 50 |
| Trans of p-beta-3 | .......... | .......... | .......... | .......... | .......... | 50 |
| Trans of p-beta-5 | .......... | .......... | .......... | .......... | .......... | 50 |
| Trans of p-beta-6 | .......... | .......... | .......... | .......... | .......... | 50 |
| | | | | | | |
| Consensus | ALPQVVCNYR | DVRFESIRLP | GCPRGVNPVV | SYAVALSCQC | ALCRRSTTDC | 100 |
| Trans of p-beta-7 | .......... | .......... | .......... | .......... | .......... | 100 |
| Trans of p-beta-8 | .......... | .......... | .......... | .......... | .......... | 100 |
| Trans of p-beta-9 | .......... | .......... | .......... | .......... | .......... | 100 |
| Trans of p-beta-3 | .......... | .......... | .......... | .......... | .......... | 100 |
| Trans of p-beta-5 | .......... | .......... | .......... | .......... | .......... | 100 |
| Trans of p-beta-6 | .......... | .......... | .......... | .......... | .......... | 100 |
| | | | | | | |
| Consensus | GGPKDHPLTC | DDPRFQDSSS | SKAPPPSLPS | PSRLPGPSDT | PILPQ | 145 |
| Trans of p-beta-7 | .......... | ......A... | .......... | .......... | ..... | 145 |
| Trans of p-beta-8 | .......... | .......... | .......... | .......... | ..... | 145 |
| Trans of p-beta-9 | .......... | .......... | .......... | .......... | ..... | 145 |
| Trans of p-beta-3 | .......... | .......... | .......... | .......... | ..... | 145 |
| Trans of p-beta-5 | .......... | .......... | .......... | .......... | ..... | 145 |
| Trans of p-beta-6 | .......... | ......A... | .......... | .......... | ..... | 145 |

FIGURE 2

US 6,514,708 B2

PROCESS FOR DETECTING THE MALIGNANT TRANSFORMATION OF HUMAN CELLS

CROSS REFERENCE TO RELATED APPLICATIONS

This application is a continuation of application Ser. No. 09/142,320, filed Sep. 4, 1998, now U.S. Pat. No. 6,194,154, which is the National Stage of International Application No. PCT/FR97/00361, filed Feb. 28, 1997.

FIELD OF THE INVENTION

The present invention relates to a process for detecting the malignant transformation of cells and its application for diagnosing and monitoring cancers and for developing cancer prognosis.

BACKGROUND OF THE INVENTION

Chorionic gonadotropic hormone (hCG) is a glycoprotein which is formed from two subunits which are termed alpha (hCGα) and beta (hCGβ) and which are linked non-covalently (1). During pregnancy, the trophoblastic cells of the placenta produce the dimeric hCG and the free hCGα or hCGβ subunits which are found in substantial quantity in the serum. The development of sensitive and specific techniques for assaying hCG and, independently, for assaying the free hCGα subunit and the free hCGβ subunit, made it possible to show that serum levels of hCG of up to 1000 pg/ml and serum levels of the free hCGα subunit of up to 3000 pg/ml were present in non-pregnant healthy subjects (2,3). It was also observed that serum levels of hCG or of the free hCGα subunit greater than these normal values are principally to be found in patients having a testicular or ovarian tumor of trophoblastic origin.

By contrast, only low serum levels of the free hCGβ subunit, i.e. which are less than 100 pg/ml, can be detected in non-pregnant healthy subjects. Serum levels of free hCGβ which are greater than these normal values are found in a large number of cancer patients who are carrying a tumor of gonadal or non-gonadal origin (2). In particular, 47% of patients with cancer of the bladder, 32% of patients with cancer of the pancreas and 30% of patients with cancer of the uterine cervix have a serum level of free hCGβ which is greater than 100 pg/ml (2). In patients with cancer of the bladder, the presence of an elevated level (greater than 100 pg/ml) of free hCGβ is reported to be correlated with unfavorable development of the disease (4,5).

While the hCGα subunit is encoded by one single gene, which is located on chromosome 6q21.1-q23, the hCGβ subunit has been reported to be encoded by a family of genes which are located on chromosome 19q13.3. Following a large number of studies, it was shown that there were 7 CGβ genes, termed CGβ7 or β7, CGβ6 or β6, CGβ8 or β8, CGβ5 or β5, CGβ1 or β1, CGβ2 or β2 and CGβ33 or β3 (6). The β6 and β7 genes are allelic (7).

Only the β7, β6, β8, β5 and β3 genes are able to encode the hCGβ subunit, which is made up of 145 amino acids. The β1 and β2 genes are characterized by the presence:

of an insertion of approximately 770 nucleotides in the 5' part of the CGβ genes, of a point mutation of the 5' splicing site of the first intron of the CGβ genes.

It has been shown that the β1 and β2 genes are capable of being transcribed in some tissues and would be able to encode a protein of 132 amino acids having a different sequence from that of hCGβ (7).

Sequencing all or part of the β7, β6, β5 and β3 genes, and the restriction maps, showed that the nucleotides corresponding to codons 2, 4 and 117 with respect to the mature CGβ protein were different depending on the genes in question (8, 9, 10).

Analysis of the nucleotide sequences for equivalent positions was carried out in the case of the β2 gene and it was shown that the gene exhibited the same characteristics as the β6 gene. On the other hand, only position 117 of the β1 gene was deduced by restriction map analysis and was regarded as being "of the Asp type".

In addition, expression of the different CGβ genes in placental tissue has been analyzed in a semiquantitative manner. The results demonstrate that the β5 transcripts are in much higher abundance than the β3 and β8 transcripts. The β7, β1 and β2 transcripts are very much in the minority (7). Finally, several studies have been carried out with the aim of looking for CGβ transcripts in various normal or neoplastic nontrophoblastic tissues or on various cell lines derived from cancerous tissues of trophoblastic or nontrophoblastic origin (11–17). The techniques employed in these different studies did not distinguish between the β7, β8, β5 and β3 transcripts. These studies demonstrated that β7, β8, β5 or β3 transcripts are present, in particular, in normal testes (11), neoplastic testes (12), neoplastic bladder (13), normal placenta, choriocarcinomic placental cell lines (14–16) and in various cells lines derived from neoplastic nontrophoblastic cells (15–17).

Recently, a study was carried out on normal and neoplastic tissues of vesical origin for the purpose of quantifying the β7, β8, β5 and β3 transcripts. This study was based on the profile observed after amplifying exons 1 and 2 and enzymatically cleaving in nucleotide positions corresponding to the 5' transcribed, untranslated part of exon 1 (18). This study demonstrated that normal vesical tissue only expresses the β7 gene and that malignant transformation of vesical tissue is accompanied by acquisition of the ability to express the β8 and/or β5 and/or β3 genes in 45 to 95% of cases (18).

SUMMARY OF THE INVENTION

The present invention is based on demonstrating the importance of the β3, β5, β8 and β9 genes in the progression to malignancy, in particular as compared with the expression, which exists in normal tissues, of the products of the β6 and β7 genes.

The present invention relates to a process for detecting the malignant transformation of human cells, characterized in that overexpression of the products of the β3, β5, β8 and/or β9 genes, encoding the hCGβ subunit, as compared with their expression in nonmalignant cells, is demonstrated in the said cells.

DETAILED DESCRIPTION OF THE PREFERRED EMBODIMENTS

It is important to note that the β9 gene, which is allelic with the β3 gene, is described below for the first time and that, like the β3, β5 and β8 genes, it leads to the synthesis of an hCGβ subunit whose 117 position is an aspartic acid and is involved in the malignant process.

"Expression products of the β3, β5, β8 and/or β9 genes" is understood as signifying both the natural mRNA transcription products and the natural translation products, that is hCGβ.

While it is of interest to demonstrate the products of these β3, β5, β8 and β9 genes, and their overexpression as compared with that in normal tissues or as compared with predetermined standards, it can be even more interesting to demonstrate variation in an index which involves the ratio between the expression products of the β3, β5, β8 and β9 genes and the totality of the same expression products for all the β genes in the same tissues.

This index, termed the "transformation index" will be explained in detail in that which follows.

The transcripts of the β genes, that is to say the mRNAs, will be demonstrated in a first embodiment of the process according to the invention.

It is possible to consider measuring the transcripts of the β3, β5, β8 and β9 genes separately or to consider assaying them in a group according to their nucleotide structure. Nevertheless, it is possible to take advantage, in these genes, of the existence of a GAC sequence, encoding aspartic acid, in position 117, which position is located at 774 to 776 and whose 775 position differs from the corresponding position of the β6 and β7 genes, encoding Ala117, by one single nucleotide, with A being replaced by C. The positions are indicated with respect to the mature mRNA, with the transcription initiation site being numbered +1. The results in the literature concerning the precise position of the initiation of the transcription of the CGβ genes are contradictory. That proposed by Otani et al. (19) has been used. The expression product of the β6 and β7 genes and present in normal cells.

It is therefore possible to demonstrate overtranscription of the transcripts of the β3, β5, β8 and β9 genes by simply measuring the overtranscription of the β gene transcripts which contain an A in position 775.

This demonstrates the presence of the transcripts of the β3, β5, β8 and/or β9 genes, which contain the sequence encoding aspartic acid in position 774 to 777.

In order to eliminate the problems associated with assay methods to the greatest possible extent, preference is given to using the transformation index which measures the ratio between the transcripts containing an A in position 775 and the totality of the β gene transcripts, that is:

$$CG117 \text{ index} = \frac{GA^{775}C \text{ transcripts}}{GA^{775}C \text{ transcripts} + GC^{775}C \text{ transcripts}} \times 100$$

In general, determination of the transcripts requires an amplification step, although this may not be necessary.

This nucleotide assay can be carried out by means of amplification methods, either on transcribed RNA or, more conveniently, on cDNA following reverse transcription of the mRNAs, and using the PCR method, for example.

More specifically, in order to demonstrate overexpression of the transcripts in this process;
(a) the total mRNAs are first of all subjected to reverse transcription,
(b) the cDNAs of the genes encoding the β subunit of hCG, and more specifically the fragments carrying the 774 to 776 sequence, are selectively amplified, and
(c) the presence of amplification products which contain an A in position 775 is demonstrated, with the result being compared with that obtained by the same assay carried out on normal tissues or with reference to standards.

Preference is also given to demonstrating, in step (c), the presence of amplification products which contain a C in position 775 and calculating the transformation index. The variation in this index in comparison with normal tissues or with standards provides a diagnosis or a prognosis with regard to the transition to the malignant stage.

Following amplification, visualization can be effected by elongating the amplification products using labeled primers, with one of the primers containing a C at the 3' end and at the position corresponding tQ nucleotide 775 and with the other containing an A in the same position and having a different label.

Extension products corresponding to the presence of an A in position 775 and, respectively, to the presence of a C in position 775 are thereby obtained. Thus, when there is no possible pairing of the primer and the amplification product at the 3' end, it is very difficult to achieve extension, as will be explained in more detail in the examples.

It is thus possible to measure the A775 hCGs and the sum of the A775 and C775 products in one single operation.

It is also possible to use different methods of the LCR or NASBA type or even direct hybridization techniques which can be adapted to the previously described principles.

Implementation of this process has demonstrated that, while, with the exception of the placenta, the index is equal to 0% in most healthy tissues in which it is possible to detect CGβ transcripts by means of RT-PCR, malignant transformation of tissues can be accompanied by an increase in this index. In particular, an increase in the index was observed in high-incidence cancers such as colon cancer, breast cancer, bladder cancer, prostate cancer and thyroid cancer, for example.

While the previous method is the method of choice for implementing the process, it is also possible to envisage demonstrating the translation products of the genes in question.

It is possible to demonstrate overexpression of the products of the β3, β5, β8 and 09 genes by demonstrating the presence of an hCGβ which carries aspartic acid in position 117 with the aid of a monoclonal antibody which is specific for the corresponding epitope. This is because the β7 and β6 genes, which are not labels of neoplastic transformation, encode an hCGβ which exhibits an alanine in position 117 and which therefore possesses a different epitope. Thus, "specific antibody" is intended to signify an antibody which recognizes the Asp117 epitope but does not recognize the Ala117 epitope.

The demonstration can be effected by means of one of the known methods of immunology, such as ELISA, RIA or IRMA, for example.

As before, it can be worthwhile, in order to avoid possible problems linked to assay peculiarities, to carry out this measurement in the form of a transformation index which, as before, would be the ratio between the measurement carried out on position Asp117 (hCGβ) and the measurement of total (hCGβ).

The process according to the invention, in particular in its nucleotide assay form, has the advantage of being based on a simple genetic change which is very strongly correlated with the malignant phenotype.

A particularly interesting feature of this test is that it can be carried out on a small number of exfoliated cells.

This test can be both quantitative and qualitative, and is simple and sensitive; it can be carried out in less than 3 hours.

It enables an early diagnosis to be made of most high-incidence cancers using a very wide variety of samples:
biopsy in the case of mammary cancer and prostate cancer,
stools in the case of cancer of the colon,
vaginal secretions (ovarian cancer),
urine (bladder cancer),
expectorate (lung cancer),
whole blood (circulating blood mononucleated cells for diagnosing circulating neoplastic cells).

The qualitative assay also enables the stage of the tumor, and its prognosis, to be evaluated.

In order to better understand the examples below, the following diagram summarizes the organization of the hCGβ genes:

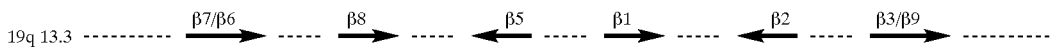

and Table 1 below assembles the information on these different genes.

Transcription and translation of the β1 and β2 genes, if they exist, do not lead to the synthesis of an hCGβ subunit of 145 amino acids.

The β3, β5, β8 and β9 genes lead to the synthesis of an hCGβ subunit of 145 amino acids which has an aspartic acid residue in position 117.

The β6 and β7 genes lead to the synthesis of an hCGβ subunit of 145 amino acids which has an alanine residue in position 117.

TABLE 1

| Codons | Genes | | | | | | | |
|---|---|---|---|---|---|---|---|---|
| | β7 | β6 | β8 | β5 | β1 | β2 | β3 | β9 |
| 2 | AGG | AAG | AAG | AAG | AAG | AAG | AAG | AAG |
| | Arg | Lys | Lys | Lys | | | Lys | Lys |
| 4 | ATG | CCA | CCG | CCG | CCG | CCG | CCG | CCG |
| | Mer | Pro | Pro | Pro | | | Pro | Pro |
| 117 | GCC | GCC | GAC | GAC | GCC | GAC | GAC | GAC |
| | Ala | Ala | Asp | Asp | | | Asp | Asp |

NB: The data in the boxes are novel findings

In that which follows, the sequence references correspond to FIGS. 1a, 1b and 1c, which depict the nucleotide sequences of the cDNAs of the hCGβ genes, and FIG. 2, which depicts the sequences of the mature hCGβ proteins.

The examples below demonstrate other characteristics and advantages of the process according to the present invention.

Materials and Methods

Extraction of the Total RNAs

The total RNAs were extracted using the method of Chomczynski and Sacchi (20). The total RNAs were quantified by UV spectrophotometry at 260 nm (with 1 OD unit corresponding to 40 µg of RNA/ml). The quality of the RNAs was assessed by visualizing the bands corresponding to the 18S and 28S ribosomal RNAs following electrophoresis on a 1% agarose gel and staining with ethidium bromide. The total RNAs were stored in DEPC water at −80° C.

Choice of Oligonucleotide Primers

Analysis of the sequences of the different genes of the hCG/LHβ multigene group made it possible to select a pair of oligonucleotide primers which amplified the CGβ3, β5, β6, β7, β8 and β9 transcripts selectively and with the same efficiency.

The following are the nucleotide sequences of the two primers (the positions are shown with reference to the mature mRNA, with the transcription initiation site being numbered+1).

Primer CGI (532–551) (SEQ ID NO: 17)
5'-GCTACCTGCCCCACCATGACC-3'

Primer CGII (878–857) (SEQ ID NO: 18)
5'-CGGGATTGAGAAGCCTTTATTGT-3'

Using total RNA and RT-PCR, these primers amplify a fragment of 347 nucleotides.

In order to rule out amplification of the genomic DNA which contaminated the RNA preparations, the CGI primer was placed in a region corresponding to the junction of exons 2 and 3. The last three nucleotides of primer CGI correspond to the first three bases of exon 3: ACC. However, the sequence of the first three bases of intron 2 is GTG in the case of the CGβ1, β2, β3, β5, β6, β7, β8, β9 and LHβ genes.

CGβ1, β2, β3, β5, β6, β7, β8 and β9 RNA (SEQ ID NOS 19 & 20):

```
       Exon 2          Exon 3
5'...GGC TAC TGC CCC ACC ATG ACC...3'
     Gly Tyr Cys Pro Thr Met Thr
```

CGβ31, β2, β3, β5, β6, β7, β8, β9 and LHβ genomic DNA (SEQ ID NOS 23 & 24):

```
       Exon 2          Intron 2
5'...GGC TAC TGC CCC ACC ATG gtg...3'
     Gly Tyr Cys Pro Thr Met
```

The use of the CGI primer also makes it possible to rule out amplification of any LHβ RNA which may be present. This is because the last three bases of the CGI primer correspond to the triplet ACC, which encodes the threonine 42 residue of the mature CGβ protein. However, the β subunit of LH possesses a methionine residue, encoded by the triplet ATG, in position 42.

CGβ1, β2, β3, β5, β6, β7, β8 and β39 RNA (SEQ ID NOS 19 & 20):

```
       Exon 2          Exon 3
5'...GGC TAC TGC CCC ACC ATG ACC...3'
     Gly Tyr Cys Pro Thr Met Thr
```

LHβ RNA (SEQ ID NOS 23 & 24):

```
       Exon 2          Exon 3
5'...GGC TAC TGC CCC ACC ATG ATG...3'
     Gly Tyr Cys Pro Thr Met Met
```

Reverse Transcription (RT) Reaction

1 µg of total RNA from each sample was reverse-transcribed in a volume of 20 µl using the Ampli Gene RNA PCR kit (Perkin-Elmer) in accordance with the manufacturer's instructions. The reaction mixture for each sample contains 20 units of reverse transcriptase, 50 units of RNAse inhibitor, 2.5 mM oligodT, 1 mM of each deoxyribonucleotide triphosphate (dA, dT, dC and dG), 10 mM DTT, 10 mM Tris-HCl (pH 8.3), 50 mM KCl and 5 mM MgCl2. The reaction mixtures are incubated consecutively in a "DNA thermal cycler" 9600 (Perkin-Elmer) for 10 minutes at 20° C. (hybridization of the oligodT), 30 minutes at 42° C. (reverse transcription) and 5 minutes at 99° C. (denaturation of the reverse transcriptase and of the RNAse inhibitor), after which they are cooled rapidly to 4° C.

Amplification Reaction (PCR)

The equivalent of 500 ng of cDNA (10 µl of the RT product) from each sample, and a negative control verifying the absence of cross contamination by amplification products, were amplified in a final volume of 50 µl containing 2.5 units of Taq polymerase (Perkin-Elmer), 200 mM of each deoxyribonucleotide triphosphate (dA, dT, dC and dG), 10 pmol of each of the CGI and CGII primers, 10 mM Tris-HCl (pH 8.3), 50 mM KCl and 1.5 mM MgCl2. The amplification was carried out in a "DNA thermal cycler 9600" (Perkin-Elmer) for 35 cycles, with each cycle comprising 30 seconds at 95° C., 30 seconds at 65° C. and 30 seconds at 72° C. The quality of the PCR was verified by electrophoresis on an 8% acrylamide gel and visualization of the amplification products by UV transillumination following staining with ethidium bromide.

Characterization of Position 775 in the hCGβ cDNAs

Comparison of the cDNA sequences of the genes encoding the hCGβ subunit enabled us to demonstrate that the β6 and β7 transcripts possess a cytosine residue in position 775 whereas the β3, β5, β8 and β9 transcripts possess an adenine residue in position 775.

A strategy was therefore worked out which made it possible to distinguish between these two types of transcript by analyzing the 775 position. This strategy is based on analyzing the amplification products of the hCGβ transcripts by means of the competitive oligonucleotide priming or COP technique (21, 22, 23). This method was initiated at the end of the 1990s and is based on using a mixture of two oligonucleotides whose characteristics are as follows:

nucleotide sequence: identical with the exception of the 3' base, which is either a cytosine residue (oligonucleotide CGIII) or an adenine residue (oligonucleotide CGIV);

5' labeling:. the oligonucleotide CGIII is labeled 5' with the fluorophore TET while the oligonucleotide CGIV is labeled 5' with the fluorophore FAM.

CGIII (SEQ ID NO: 1): 5'-TET-ACCCCCGCTTCCAGGC-3'

CGIV (SEQ ID NO: 2): 5'-FAM-ACCCCCGC-TTCCAGGA-3'.

The extension efficiency using one primer is strictly dependent on the 3' pairing. When there is a 3' mispairing, the extension efficiency is very much diminished, particularly when the mispairing is of the A:G, G:A, C:C or G:G type (23).

It was shown that it is possible to improve the specificity and, at the same time, the sensitivity of the COP technique by replacing the Taq polymerase with the Stoffel fragment (24). In addition, some parameters were optimized: quantity of RT-PCR products, quantity of oligonucleotides, concentration of $Mg^{2+}$ and of dNTPs, nature and number of cycles (25).

The COP reaction is carried out in a volume of 10 µl using 1 µl of RT-PCR diluted 1/20 in distilled water. The reaction contains 2 units of Taq polymerase, Stoffel fragment (Perkin-Elmer), 50 pH of each deoxyribonucleotide triphosphate (dA, dT, dC and dG), 0.1 pmol of each of the two oligonucleotides CGIII and CGIV, 10 mM Tris-HCl (pH 8.3), 10 mM KCl and 1.5 mM $MgCl_2$. This reaction is carried out in a "DNA thermal cycler 9600" (Perkin-Elmer) over 5 cycles, each of which comprises 30 seconds at 95° C. and 30 seconds at 65° C. The COP products which are obtained are analyzed on an automated DNA sequencer (Perkin-Elmer, model 373A): 2.5 µl of COP product are mixed with 2 µl of blue loading buffer and 0.5 µl of Genescan 2500 ROX size marker (Perkin-Elmer) and then subjected to a 1 hour electrophoresis in 1×TBE buffer (2500 V, 40 mA, 30 W) in a denaturing gel (8% acrylamide, 6 M urea, 1×TBE).

The results are then analyzed using Genscan 672 software (Perkin-Elmer), which not only makes it possible to differentiate the fragments on the basis of their size and the nature of the fluorophore attached to the 5' end of the primer, but also to calculate, for each peak, a surface area which is directly proportional to the number of molecules which are present in the COP product.

Thus, the presence of a 119 base pair fragment which is labeled 5' with TET indicates the presence of transcripts which are carrying a cytosine residue in position 775. On the other hand, the presence of a 119 base pair fragment which is labeled 5' with FAM indicates the presence of transcripts which are carrying an adenine residue in position 775.

This approach has two major advantages:

This is a very sensitive method since it is possible to increase the number of cycles of the COP reaction and thereby to detect a small number of cells which are expressing the transcripts which carry an adenine residue in position 775, with this being ever more the case since the 3' mispairing is of the A:G type, that is to say the mispairing is that which is most unfavorable for achieving a primer extension.

This method is quantitative as well as being qualitative. Table 2 assembles the results of an experiment which was carried out using a mixture, in known proportion, of 2 RT-PCR products which were derived, respectively, from a healthy tissue which was only expressing the cytosine 775 transcripts (samples 1, 2 and 3) and a neoplastic tissue which was mainly expressing the adenine 775 transcripts (samples 16, 17 and 18). For each point, the experiment was carried out in triplicate.

TABLE 2

| Samples | $GC^{775}C$ Transcript (CGIII) | $GA^{775}C$ Transcript (CGIV) | Index* |
|---|---|---|---|
| 1 | 20.428 | — | 0 |
| 2 | 22.174 | — | 0 |
| 3 | 25.875 | — | 0 |
| 4 | 15.653 | 2.237 | 12 |
| 5 | 21.960 | 3.414 | 12 |
| 6 | 20.968 | 3.192 | 13 |
| 7 | 16.587 | 5.987 | 26 |
| 8 | 17.438 | 5.923 | 25 |
| 9 | 15.567 | 5.371 | 25 |
| 10 | 13.962 | 10.308 | 42 |
| 11 | 12.117 | 9.335 | 43 |
| 12 | 9.556 | 7.859 | 45 |
| 13 | 8.203 | 13.784 | 62 |
| 14 | 8.076 | 13.335 | 62 |
| 15 | 8.072 | 13.624 | 62 |
| 16 | 503 | 18.779 | 97 |
| 17 | 440 | 15.879 | 97 |
| 18 | 635 | 18.203 | 96 |

*Index expressed as previously described

The results demonstrate that the reproducibility is excellent and that there is proportionality between the quantities of the 775A and 755C transcripts and the index.

Some cancers have been assessed, and Table 3 gives the preliminary results obtained in relation to breast cancer, bladder cancer, thyroid cancer, prostate cancer and colon cancer.

TABLE 3

|  |  | CG 117 Index | |
|---|---|---|---|
|  |  | Negative Index = 0 | Positive Index > 0 |
| Breast | Normal: n = 11 | 11 (100%) | 0 (0%) |
|  | Neoplastic: n = 102 | 58 (57%) | 44 (43%) |
| Bladder | Normal: n = 4 | 4 (100%) | 0 (0%) |
|  | Neoplastic: n = 34 | 13 (38%) | 21 (62%) |
| Thyroid | Adenoma: n = 15 | 15 (100%) | 0 (0%) |
|  | Carcinoma: n = 12 | 9 (75%) | 3 (25%) |
| Prostate | Normal: n = 4 | 4 (100%) | 0 (0%) |
|  | Neoplastic: n = 3 | 2 (66%) | 1 (33%) |
| Colon | Normal: n = 1 | 1 (100%) | 0 (0%) |
|  | Neoplastic: n = 2 | 1 (50%) | 1 (50%) |

LITERATURE

1—Pierce J. G., Parsons T. F., *Annu. Rev. Biochem.,* 50, 465–495 (1981).
2—Marcillac I. et al., *Cancer Res.,* 52, 3901–307 (1992).
3—Alfthan H., Haglund C., Dabek J. & Stenman U. H., *Clin. Chem.,* 38, 1981–1987 (1992).
4—Marcillac I., Cottu P., Theodore C., Terrier-Lacombe M., Bellet D. & Droz J-P, *Lancet,* 341, 1354–1355 (1993).
5—Iles R. K., Jenkins B. J., Oliver R. T. D., Blandy J-P & Chard T., *Br. J. Urol.,* 64, 241–244 (1989).
6—Jameson L. J. & Hollenberg A. N., *Endocrinol. Rev.,* 14, 203–221 (1993).
7—Bo M. & Boime I., *J. Biol. Chem.,* 267, 3179–3184 (1992).
8—Talmadge K., Vamvakopoulos N. C. & Fiddes J. C., *Nature,* 307, 37–40 (1984).
9—Talmadge K., Boorstein W. R., Vamvakopoulos N. V., Gething M. J. & Fiddes J. C., *Nucleic. Acids Res.,* 12, 8415–8436 (1984).
10—Policastro P., Ovitt C. E., Hoshina M., Fukuoka H., Boothby M. R. & Boime I., *J. Biol. Chem.,* 258, 11492–11499 (1983).
11—Berger P., Kranewitter W., Madersbacher S., Gerth R., Geley S. & Dirnhofer S., *FEBS Lett.,* 343, 229–233 (1994).
12—Madersbacher S., Kratzik C., Gerth R., Dirnhofer S. & Berger P., *Cancer Res.,* 54, 5096–5100 (1994).
13—Oyasu R., Nan L., Smith P. & Kawamata H., *Arch. Pathol. Lab. Med.,* 119, 715–717 (1994).
14—Jameson L., Lindell C. M. & Habener J. F., *J. Clin. Endocrinol. Metab.,* 64, 319–327 (1986).
15—Acevedo H. F., Tong J. Y. & Hartsock R. J., *Cancer,* 76, 1467–1475 (1995).
16—Cosgrove D. E., Campain J. A. & Cos G. S., *Biochim. Biophys. Acta.,* 1007, 44–54 (1989).
17—Campain J. A., Gutkin D. W. & Cox G. S., *Mol. Endocrinol.,* 7, 1331–1346 (1993).
18—Lazar V. et al., *Cancer Res.,* 55, 3735–3738 (1995).
19—Otani T., Otani F., Krych M., Chaplin D. D., Boime I., *J. Biol. Chem.,* 263, 7322–7329 (1988).
20—Chomczynski P. & Sacchi N., *Anal. Biochem.,* 162, 156–159 (1987).
21—Gibbs R. A., Nguyen P. N., Caskey C. T., *Nucleic Acids Res.,* 17, 2437–2448 (1989).
22—Chehab F. F. & Kan Y. W., *Proc. Natl. Acad. Sci. USA,* 86, 9178–9182 (1989).
23—Huang M. M., Arnheim N., Goodman M. F., *Nucleic Acids Res.,* 20, 4567–4573 (1992).
24 Tada M., Omata M., Kawai S., Saisho H., Ohto M., Saiki R. K., Sninsky J. J., *Cancer Res.,* 53, 2472–2474 (1993).
25—Rychlik W., *Biotechniques,* 1, 84–89 (1995).

What is claimed is:

1. A method for detecting the malignant transformation of human cells, comprising detecting in malignant cells the overexpression of the translation products of the β03, β5, β8, and β9 genes, encoding the hCGβ subunits, compared with their expression in nonmalignant cells.

2. The method according to claim 1, wherein the increase in the ratio between the expression of the translation products of the β3, β5, β8, and β9 genes and the expression of the translation products of the totality of the β genes is detected in the malignant cells.

3. The method according to claim 1, wherein the overexpression of the hCGβ protein that contains an aspartic acid residue in position 117 is detected.

4. The method according to claim 3, wherein the production of the hCGβ protein that contains an aspartic acid residue at position 117 is detected by binding a monoclonal antibody that is specific for an epitope that contains an aspartic acid in position 117.

5. The method according to claim 4, wherein overexpression of translation products that contain an aspartic acid residue in position 117, compared with the totality of the translation products from the genes encoding the β subunits, is detected.

6. The method according to claim 3, wherein the increase in the index of the translation products that contain an aspartic acid residue in position 117, compared with the totality of the hCGβ subunit translation products, is assessed.

* * * * *

SEQUENCE LISTING

```
<160> NUMBER OF SEQ ID NOS: 24

<210> SEQ ID NO 1
<211> LENGTH: 16
<212> TYPE: DNA
<213> ORGANISM: primer

<400> SEQUENCE: 1 accccgctt ccaggc                                                      16

<210> SEQ ID NO 2
<211> LENGTH: 16
<212> TYPE: DNA
<213> ORGANISM: primer

<400> SEQUENCE: 2 accccgctt ccagga                                                      16

<210> SEQ ID NO 3
<211> LENGTH: 893
<212> TYPE: DNA
<213> ORGANISM: human
<220> FEATURE:
<223> OTHER INFORMATION: consensus sequence

<400> SEQUENCE: 3
tccagcacyt tbctcgggtc acggcctcct cctggytycc argacccac cataggcaga       60 ggcaggcctt cctacaccct actcyctgtg cctccagsct ygactagtcc ctarcactcg     120
```

```
acgactgagt ctcwgagrtc acttcaccgt ggtctccgcc tcayccttgg ygctrgacca      180
stgagrggag aggrctgggg ygctccgctg agccactcct ghgccyccst ggccttgtct      240
acytctygcc ccccrarggg ttagtgtcsa gctcaccyca gcatcctaym acctcctggt      300
ggccttgmcg cccccacaam cccgaggtwt raagccaggt acacsaggca gggacrcac       360 caaggatgga gatgttccag gggctgctgc tgttgctgct gctgagcatg ggcgggacat      420
gggcatccar ggagmyrctt cggccacggt gccgcccat caatgccacc ctggctgtgg      480
agaaggaggg ctgccccgtg tgcatcaccg tcaacaccac catctgtgcc ggctactgcc      540
ccaccatgac ccgcgtgctg cagggggtcc tgccggccct gcctcaggtg gtgtgcaact      600
accgcgatgt gcgcttcgag tccatccggc tccctggctg cccgcgcggc gtgaaccccg      660
tggtctccta cgccgtggct ctcagctgtc aatgtgcact ctgccgccgc agcaccactg      720
actgcggggg tccaaggac caccccttga cctgtgatga ccccgcttc caggmctcct        780 cttcctcaaa ggcccctccc ccsagccttc aagyccatc ccgactcccg ggccctcgg       840 acaccccgat cctcccacaa taaaggcttc tcaatccgca ctctggmggt gtc             893
```

<210> SEQ ID NO 4
<211> LENGTH: 145
<212> TYPE: PRT
<213> ORGANISM: human
<220> FEATURE:
<223> OTHER INFORMATION: consensus sequence
<223> OTHER INFORMATION: Xaa at postition 2 is a Lys or Arg
<223> OTHER INFORMATION: Xaa at position 4 is a Pro or Met
<223> OTHER INFORMATION: Xaa at position 117 is an Ala or Asp

<400> SEQUENCE: 4

Ser Xaa Glu Xaa Leu Arg Pro Arg Cys Arg Pro Ile Asn Ala Thr Leu
 1               5                  10                  15

Ala Val Glu Lys Glu Gly Cys Pro Val Cys Ile Thr Val Asn Thr Thr
                20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
        50                  55                  60

Glu Ser Ile Arg Leu Pro Gly Cys Pro Arg Gly Val Asn Pro Val Val
 65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Xaa Ser Ser Ser Lys Ala Pro Pro Pro Ser Leu
        115                 120                 125

Pro Ser Pro Ser Arg Leu Pro Gly Pro Ser Asp Thr Pro Ile Leu Pro
    130                 135                 140

Gln
145

<210> SEQ ID NO 5
<211> LENGTH: 893
<212> TYPE: DNA
<213> ORGANISM: human

<400> SEQUENCE: 5
tccagcacct ttctcgggtc acggcctcct cctggttccc aagacccac cataggcaga        60

```
ggcaggcctt cctacaccct actctctgtg cctccagcct cgactagtcc ctagcactcg    120
acgactgagt ctcagaggtc acttcaccgt ggtctccgcc tcatccttgg tgctagacca    180
ctgaggggag aggactgggg tgctccgctg agccactcct gtgcctccct ggccttgtct    240
acttctcgcc ccccgaaggg ttagtgtcca gctcactcca gcatcctaca acctcctggt    300
ggccttgacg cccccacaaa cccgaggtat aaagccaggt acaccaggca ggggacgcac    360
caaggatgga gatgttccag gggctgctgc tgttgctgct gctgagcatg ggcgggacat    420
gggcatccag ggagatgctt cggccacggt gccgcccat caatgccacc ctggctgtgg    480
agaaggaggg ctgccccgtg tgcatcaccg tcaacaccac catctgtgcc ggctactgcc    540
ccaccatgac ccgcgtgctg caggggggtcc tgccggccct gcctcaggtg gtgtgcaact    600
accgcgatgt gcgcttcgag tccatccggc tccctggctg cccgcgcggc gtgaaccccg    660
tggtctccta cgccgtggct ctcagctgtc aatgtgcact ctgccgccgc agcaccactg    720
actgcggggg tcccaaggac cacccttga cctgtgatga ccccgcttc caggcctcct    780 cttcctcaaa ggcccctccc cccagccttc caagtccatc ccgactcccg ggccctcgg    840 acaccccgat cctcccacaa taaaggcttc tcaatccgca ctctggaggt gtc          893

<210> SEQ ID NO 6
<211> LENGTH: 893
<212> TYPE: DNA
<213> ORGANISM: human

<400> SEQUENCE: 6
tccagcactt tcctcgggtc acggcctcct cctggttccc aagaccccac cataggcaga    60
ggcaggcctt cctacaccct actctctgtg cctccagcct cgactagtcc ctaacactcg    120
acgactgagt ctcagaggtc acttcaccgt ggtctccgcc tcatccttgg cgctagacca    180
ctgaggggag aggactgggg tgctccgctg agccactcct gtgcctccct ggccttgtct    240
acttctcgcc ccccgaaggg ttagtgtcga gctcactcca gcatcctaca acctcctggt    300
ggccttgccg cccccacaac cccgaggtat gaagccaggt acaccaggca ggggacgcac    360
caaggatgga gatgttccag gggctgctgc tgttgctgct gctgagcatg ggcgggacat    420
gggcatccaa ggagccactt cggccacggt gccgcccat caatgccacc ctggctgtgg    480
agaaggaggg ctgccccgtg tgcatcaccg tcaacaccac catctgtgcc ggctactgcc    540
ccaccatgac ccgcgtgctg caggggggtcc tgccggccct gcctcaggtg gtgtgcaact    600
accgcgatgt gcgcttcgag tccatccggc tccctggctg cccgcgcggc gtgaaccccg    660
tggtctccta cgccgtggct ctcagctgtc aatgtgcact ctgccgccgc agcaccactg    720
actgcggggg tcccaaggac cacccttga cctgtgatga ccccgcttc caggcctcct    780 cttcctcaaa ggcccctccc cccagccttc caagtccatc ccgactcccg ggccctcgg    840 acaccccgat cctcccacaa taaaggcttc tcaatccgca ctctggaggt gtc          893

<210> SEQ ID NO 7
<211> LENGTH: 893
<212> TYPE: DNA
<213> ORGANISM: human

<400> SEQUENCE: 7
tccagcacct ttctcgggtc acggcctcct cctggctccc aggaccccac cataggcaga    60
ggcaggcctt cctacaccct actccctgtg cctccagcct cgactagtcc ctagcactcg    120
```

```
acgactgagt ctctgaggtc acttcaccgt ggtctccgcc tcacccttgg cgctggacca      180
gtgagaggag agggctgggg cgctccgctg agccactcct gcgcccccct ggccttgtct      240
acctcttgcc ccccgagggg ttagtgtcga gctcacccca gcatcctatc acctcctggt      300
ggccttgccg cccccacaac cccgaggtat aaagccaggt acacgaggca ggggacgcac      360
caaggatgga gatgttccag gggctgctgc tgttgctgct gctgagcatg ggcgggacat      420
gggcatccaa ggagccgctt cggccacggt gccgcccat caatgccacc ctggctgtgg       480
agaaggaggc tgccccgtg tgcatcaccg tcaacaccac catctgtgcc ggctactgcc       540
ccaccatgac ccgcgtgctg caggggtcc tgccggccct gcctcaggtg tgtgcaact        600
accgcgatgt gcgcttcgag tccatccggc tccctggctg cccgcgcggc gtgaaccccg      660
tggtctccta cgccgtggct ctcagctgtc aatgtgcact ctgccgccgc agcaccactg      720
actgcggggg tcccaaggac cacccttga cctgtgatga ccccgcttc caggactcct        780
cttcctcaaa ggcccctccc cccagccttc aagcccatc ccgactcccg ggccctcgg        840
acaccccgat cctcccacaa taaaggcttc tcaatccgca ctctggcggt gtc             893

<210> SEQ ID NO 8
<211> LENGTH: 893
<212> TYPE: DNA
<213> ORGANISM: human

<400> SEQUENCE: 8
tccagcacct ttctcgggtc acggcctcct cctggctccc aggaccccac cataggcaga      60
ggcaggcctt cctacaccct actccctgtg cctccaggct tgactagtcc ctagcactcg      120
acgactgagt ctctgaggtc acttcaccgt ggtctccgcc tcacccttgg cgctggacca     180
gtgagaggag agggctgggg cgctccgctg agccactcct gcgcccccct ggccttgtct     240
acctcttgcc ccccgaaggg ttagtgtcga gctcactcca gcatcctaca acctcctggt     300
ggccttgccg cccccacaac cccgaggttt aaagccaggt acacgaggca gggacacac      360
caaggatgga gatgttccag gggctgctgc tgttgctgct gctgagcatg ggcgggacat     420
gggcatccaa ggagccgctt cggccacggt gccgcccat caatgccacc ctggctgtgg      480
agaaggaggc tgccccgtg tgcatcaccg tcaacaccac catctgtgcc ggctactgcc      540
ccaccatgac ccgcgtgctg caggggtcc tgccggccct gcctcaggtg tgtgcaact       600
accgcgatgt gcgcttcgag tccatccggc tccctggctg cccgcgcggc gtgaaccccg     660
tggtctccta cgccgtggct ctcagctgtc aatgtgcact ctgccgccgc agcaccactg     720
actgcggggg tcccaaggac cacccttga cctgtgatga ccccgcttc caggactcct       780
cttcctcaaa ggcccctccc cccagccttc aagtccatc ccgactcccg ggccctcgg       840
acaccccgat cctcccacaa taaaggcttc tcaatccgca ctctggaggt gtc             893

<210> SEQ ID NO 9
<211> LENGTH: 893
<212> TYPE: DNA
<213> ORGANISM: human

<400> SEQUENCE: 9
tccagcactt tgctcgggtc acggcctcct cctggctccc aggaccccac cataggcaga      60
ggcaggcctt cctacaccct actccctgtg cctccaggct cgactagtcc ctagcactcg     120
acgactgagt ctctgagatc acttcaccgt ggtctccgcc tcacccttgg cgctggacca    180
gtgagaggag agggctgggg cgctccgctg agccactcct gcgcccccct ggccttgtct    240
```

-continued

```
acctcttgcc ccccgaaggg ttagtgtcga gctcacccca gcatcctaca acctcctggt      300
ggccttgccg cccccacaac cccgaggtat aaagccaggt acacgaggca ggggacgcac      360
caaggatgga gatgttccag gggctgctgc tgttgctgct gctgagcatg ggcgggacat      420
gggcatccaa ggagccgctt cggccacggt gccgcccat caatgccacc ctggctgtgg       480
agaaggaggg ctgccccgtg tgcatcaccg tcaacaccac catctgtgcc ggctactgcc      540
ccaccatgac ccgcgtgctg cagggggtcc tgccggccct gcctcaggtg gtgtgcaact      600
accgcgatgt gcgcttcgag tccatccggc tccctggctg cccgcgcggc gtgaaccccg      660
tggtctccta cgccgtggct ctcagctgtc aatgtgcact ctgccgccgc agcaccactg      720
actgcggggg tcccaaggac caccccttga cctgtgatga ccccgcttc caggactcct       780 cttcctcaaa ggcccctccc ccagccttc caagtccatc ccgactcccg gggccctcgg       840
acaccccgat cctcccacaa taaaggcttc tcaatccgca ctctggaggt gtc             893
```

<210> SEQ ID NO 10
<211> LENGTH: 893
<212> TYPE: DNA
<213> ORGANISM: human

<400> SEQUENCE: 10

```
tccagcactt tgctcgggtc acggcctcct cctggcttcc aagacccac catagggcaga      60 ggcaggcctt cctacaccct actccctgtg cctccagcct cgactagtcc ctagcactcg      120
acgactgagt ctctgaggtc acttcaccgt ggtctccgcc tcacccttgg cgctggacca      180
ctgaggggag agggctgggg cgctccgctg agccactcct gagcccccgt ggccttgtct      240
acctcttgcc ccccaagggg ttagtgtcga gctcacccca gcatcctacc acctcctggt      300
ggccttgccg cccccacaac cccgaggtat aaagccaggt acacgaggca ggggacgcac      360
caaggatgga gatgttccag gggctgctgc tgttgctgct gctgagcatg ggcgggacat      420
gggcatccaa ggagccgctt cggccacggt gccgcccat caatgccacc ctggctgtgg       480
agaaggaggg ctgccccgtg tgcatcaccg tcaacaccac catctgtgcc ggctactgcc      540
ccaccatgac ccgcgtgctg cagggggtcc tgccggccct gcctcaggtg gtgtgcaact      600
accgcgatgt gcgcttcgag tccatccggc tccctggctg cccgcgcggc gtgaaccccg      660
tggtctccta cgccgtggct ctcagctgtc aatgtgcact ctgccgccgc agcaccactg      720
actgcggggg tcccaaggac caccccttga cctgtgatga ccccgcttc caggactcct       780 cttcctcaaa ggcccctccc ccagccttc caagtccatc ccgactcccg gggccctcgg       840
acaccccgat cctcccacaa taaaggcttc tcaatccgca ctctggcggt gtc             893
```

<210> SEQ ID NO 11
<211> LENGTH: 145
<212> TYPE: PRT
<213> ORGANISM: human

<400> SEQUENCE: 11

```
Ser Arg Glu Met Leu Arg Pro Arg Cys Arg Pro Ile Asn Ala Thr Leu
 1               5                  10                  15

Ala Val Glu Lys Glu Gly Cys Pro Val Cys Ile Thr Val Asn Thr Thr
             20                  25                  30

Ile Cys Ala Gly Tyr Cys Pro Thr Met Thr Arg Val Leu Gln Gly Val
         35                  40                  45

Leu Pro Ala Leu Pro Gln Val Val Cys Asn Tyr Arg Asp Val Arg Phe
```

-continued

```
            50                  55                  60
Glu Ser Ile Arg Leu Pro Gly Cys Pro Arg Gly Val Asn Pro Val Val
 65                  70                  75                  80

Ser Tyr Ala Val Ala Leu Ser Cys Gln Cys Ala Leu Cys Arg Arg Ser
                 85                  90                  95

Thr Thr Asp Cys Gly Gly Pro Lys Asp His Pro Leu Thr Cys Asp Asp
                100                 105                 110

Pro Arg Phe Gln Ala Ser Ser Ser Lys Ala Pro Pro Ser Leu
             115                 120                 125

Pro Ser Pro Ser Arg Leu Pro Gly Pro Ser Asp Thr Pro Ile Leu Pro
130                 135                 140

Gln
145

<210> SEQ ID NO 12
<211> LENGTH: 145
<212> TYPE: PRT
<213> ORGANISM: human

<400> SEQUENCE: 12

Ser Lys Glu Pro Leu Arg Pro Arg Cys Arg Pro Ile Asn Ala Thr Leu
  1               5                  10                  15

Ala Val Glu Lys Glu Gly Cys Pro Val Cys Ile Thr Val Asn Thr Thr
                 20                  25                  30

Ile Cys Ala Gly Tyr Cys Pro Thr Met Thr Arg Val Leu Gln Gly Val
             35                  40                  45

Leu Pro Ala Leu Pro Gln Val Val Cys Asn Tyr Arg Asp Val Arg Phe
         50                  55                  60

Glu Ser Ile Arg Leu Pro Gly Cys Pro Arg Gly Val Asn Pro Val Val
 65                  70                  75                  80

Ser Tyr Ala Val Ala Leu Ser Cys Gln Cys Ala Leu Cys Arg Arg Ser
                 85                  90                  95

Thr Thr Asp Cys Gly Gly Pro Lys Asp His Pro Leu Thr Cys Asp Asp
                100                 105                 110

Pro Arg Phe Gln Asp Ser Ser Ser Lys Ala Pro Pro Ser Leu
             115                 120                 125

Pro Ser Pro Ser Arg Leu Pro Gly Pro Ser Asp Thr Pro Ile Leu Pro
130                 135                 140

Gln
145

<210> SEQ ID NO 13
<211> LENGTH: 145
<212> TYPE: PRT
<213> ORGANISM: human

<400> SEQUENCE: 13

Ser Lys Glu Pro Leu Arg Pro Arg Cys Arg Pro Ile Asn Ala Thr Leu
  1               5                  10                  15

Ala Val Glu Lys Glu Gly Cys Pro Val Cys Ile Thr Val Asn Thr Thr
                 20                  25                  30

Ile Cys Ala Gly Tyr Cys Pro Thr Met Thr Arg Val Leu Gln Gly Val
             35                  40                  45

Leu Pro Ala Leu Pro Gln Val Val Cys Asn Tyr Arg Asp Val Arg Phe
         50                  55                  60

Glu Ser Ile Arg Leu Pro Gly Cys Pro Arg Gly Val Asn Pro Val Val
```

```
                65                  70                  75                  80
Ser Tyr Ala Val Ala Leu Ser Cys Gln Cys Ala Leu Cys Arg Arg Ser
                    85                  90                  95

Thr Thr Asp Cys Gly Gly Pro Lys Asp His Pro Leu Thr Cys Asp Asp
                100                 105                 110

Pro Arg Phe Gln Asp Ser Ser Ser Lys Ala Pro Pro Ser Leu
            115                 120                 125

Pro Ser Pro Ser Arg Leu Pro Gly Pro Ser Asp Thr Pro Ile Leu Pro
        130                 135                 140

Gln
145

<210> SEQ ID NO 14
<211> LENGTH: 145
<212> TYPE: PRT
<213> ORGANISM: human

<400> SEQUENCE: 14

Ser Lys Glu Pro Leu Arg Pro Arg Cys Arg Pro Ile Asn Ala Thr Leu
  1               5                  10                  15

Ala Val Glu Lys Glu Gly Cys Pro Val Cys Ile Thr Val Asn Thr Thr
                20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
        50                  55                  60

Glu Ser Ile Arg Leu Pro Gly Cys Pro Arg Gly Val Asn Pro Val Val
 65                 70                  75                  80

Ser Tyr Ala Val Ala Leu Ser Cys Gln Cys Ala Leu Cys Arg Arg Ser
                    85                  90                  95

Thr Thr Asp Cys Gly Gly Pro Lys Asp His Pro Leu Thr Cys Asp Asp
                100                 105                 110

Pro Arg Phe Gln Asp Ser Ser Ser Lys Ala Pro Pro Ser Leu
            115                 120                 125

Pro Ser Pro Ser Arg Leu Pro Gly Pro Ser Asp Thr Pro Ile Leu Pro
        130                 135                 140

Gln
145

<210> SEQ ID NO 15
<211> LENGTH: 145
<212> TYPE: PRT
<213> ORGANISM: human

<400> SEQUENCE: 15

Ser Lys Glu Pro Leu Arg Pro Arg Cys Arg Pro Ile Asn Ala Thr Leu
  1               5                  10                  15

Ala Val Glu Lys Glu Gly Cys Pro Val Cys Ile Thr Val Asn Thr Thr
                20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
        50                  55                  60

Glu Ser Ile Arg Leu Pro Gly Cys Pro Arg Gly Val Asn Pro Val Val
 65                 70                  75                  80

Ser Tyr Ala Val Ala Leu Ser Cys Gln Cys Ala Leu Cys Arg Arg Ser
```

```
                        85                  90                  95
Thr Thr Asp Cys Gly Gly Pro Lys Asp His Pro Leu Thr Cys Asp Asp
            100                 105                 110
Pro Arg Phe Gln Asp Ser Ser Ser Lys Ala Pro Pro Ser Leu
            115                 120                 125
Pro Ser Pro Ser Arg Leu Pro Gly Pro Ser Asp Thr Pro Ile Leu Pro
            130                 135                 140
Gln
145

<210> SEQ ID NO 16
<211> LENGTH: 145
<212> TYPE: PRT
<213> ORGANISM: human

<400> SEQUENCE: 16

Ser Lys Glu Pro Leu Arg Pro Arg Cys Arg Pro Ile Asn Ala Thr Leu
 1               5                  10                  15
Ala Val Glu Lys Glu Gly Cys Pro Val Cys Ile Thr Val Asn Thr Thr
                20                  25                  30
Ile Cys Ala Gly Tyr Cys Pro Thr Met Thr Arg Val Leu Gln Gly Val
            35                  40                  45
Leu Pro Ala Leu Pro Gln Val Val Cys Asn Tyr Arg Asp Val Arg Phe
        50                  55                  60
Glu Ser Ile Arg Leu Pro Gly Cys Pro Arg Gly Val Asn Pro Val Val
 65                  70                  75                  80
Ser Tyr Ala Val Ala Leu Ser Cys Gln Cys Ala Leu Cys Arg Arg Ser
                85                  90                  95
Thr Thr Asp Cys Gly Gly Pro Lys Asp His Pro Leu Thr Cys Asp Asp
            100                 105                 110
Pro Arg Phe Gln Ala Ser Ser Ser Lys Ala Pro Pro Ser Leu
            115                 120                 125
Pro Ser Pro Ser Arg Leu Pro Gly Pro Ser Asp Thr Pro Ile Leu Pro
            130                 135                 140
Gln
145

<210> SEQ ID NO 17
<211> LENGTH: 21
<212> TYPE: DNA
<213> ORGANISM: primer

<400> SEQUENCE: 17
gctacctgcc ccaccatgac c                                        21

<210> SEQ ID NO 18
<211> LENGTH: 23
<212> TYPE: DNA
<213> ORGANISM: primer

<400> SEQUENCE: 18
cgggattgag aagcctttat tgt                                      23

<210> SEQ ID NO 19
<211> LENGTH: 21
<212> TYPE: DNA
<213> ORGANISM: human
<220> FEATURE:
<221> NAME/KEY: CDS
```

```
<222> LOCATION: (1)..(21)

<400> SEQUENCE: 19 ggc tac tgc ccc acc atg acc                                              21
Gly Tyr Cys Pro Thr Met Thr
 1               5

<210> SEQ ID NO 20
<211> LENGTH: 7
<212> TYPE: PRT
<213> ORGANISM: human

<400> SEQUENCE: 20

Gly Tyr Cys Pro Thr Met Thr
 1               5

<210> SEQ ID NO 21
<211> LENGTH: 21
<212> TYPE: DNA
<213> ORGANISM: human
<220> FEATURE:
<221> NAME/KEY: CDS
<222> LOCATION: (1)..(21)

<400> SEQUENCE: 21 ggc tac tgc ccc acc atg gtg                                              21
Gly Tyr Cys Pro Thr Met Val
 1               5

<210> SEQ ID NO 22
<211> LENGTH: 7
<212> TYPE: PRT
<213> ORGANISM: human

<400> SEQUENCE: 22

Gly Tyr Cys Pro Thr Met Val
 1               5

<210> SEQ ID NO 23
<211> LENGTH: 21
<212> TYPE: DNA
<213> ORGANISM: human
<220> FEATURE:
<221> NAME/KEY: CDS
<222> LOCATION: (1)..(21)

<400> SEQUENCE: 23 ggc tac tgc ccc acc atg atg                                              21
Gly Tyr Cys Pro Thr Met Met
 1               5

<210> SEQ ID NO 24
<211> LENGTH: 7
<212> TYPE: PRT
<213> ORGANISM: human

<400> SEQUENCE: 24

Gly Tyr Cys Pro Thr Met Met
 1               5
```